United States Patent
Hasegawa et al.

(10) Patent No.: US 11,051,879 B2
(45) Date of Patent: Jul. 6, 2021

(54) CONTROL DEVICE FOR SURGICAL INSTRUMENT, AND SURGICAL SYSTEM

(71) Applicant: OLYMPUS CORPORATION, Hachioji (JP)

(72) Inventors: Shogo Hasegawa, Niiza (JP); Sadayoshi Takami, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 500 days.

(21) Appl. No.: 16/014,832

(22) Filed: Jun. 21, 2018

(65) Prior Publication Data

US 2018/0296265 A1 Oct. 18, 2018

Related U.S. Application Data

(63) Continuation of application No. PCT/JP2015/085674, filed on Dec. 21, 2015.

(51) Int. Cl.
```
A61B 18/12    (2006.01)
A61B 18/14    (2006.01)
A61B 18/08    (2006.01)
A61B 18/10    (2006.01)
A61B 18/00    (2006.01)
A61B 17/00    (2006.01)
```

(52) U.S. Cl.
CPC ........ *A61B 18/1492* (2013.01); *A61B 18/085* (2013.01); *A61B 18/10* (2013.01);
(Continued)

(58) Field of Classification Search
CPC ... A61B 18/085; A61B 18/10; A61B 18/1206; A61B 18/1492; A61B 2017/00084;
(Continued)

(56) References Cited

U.S. PATENT DOCUMENTS

| | | | |
|---|---|---|---|
| 8,034,052 B2 * | 10/2011 | Podhajsky | A61B 18/1477 606/41 |
| 2006/0020313 A1 * | 1/2006 | Eggers | A61B 18/04 607/103 |
| 2014/0155877 A1 | 6/2014 | Yasunaga | |

FOREIGN PATENT DOCUMENTS

| | | |
|---|---|---|
| EP | 2 856 935 A1 | 4/2015 |
| JP | H8-213151 A | 8/1996 |

(Continued)

OTHER PUBLICATIONS

Jun. 26, 2018 International Preliminary Report on Patentability issued in International Patent Application PCT/JP2015/085674.
(Continued)

*Primary Examiner* — Michael F Peffley
*Assistant Examiner* — Amanda L Zink
(74) *Attorney, Agent, or Firm* — Oliff PLC

(57) ABSTRACT

A control device controls a surgical instrument including a heater. The control device includes a first power supply, a second power supply, a resistance value calculation section, and an output control circuit. The first power supply outputs a first current having a first frequency and supplied to the heater. The second power supply outputs a second current combined with the first current, supplied to the heater and having a second frequency different from the first frequency. The resistance value calculation section separates a signal component related to the second current from the first and second currents having passed through the heater, and calculates a heater resistance value based on the signal component. The output control circuit controls a temperature of the heater based on the heater resistance value.

12 Claims, 15 Drawing Sheets

(52) U.S. Cl.
CPC . *A61B 18/1206* (2013.01); *A61B 2017/00084* (2013.01); *A61B 2018/0063* (2013.01); *A61B 2018/00589* (2013.01); *A61B 2018/00595* (2013.01); *A61B 2018/00642* (2013.01); *A61B 2018/00702* (2013.01); *A61B 2018/00791* (2013.01); *A61B 2018/00875* (2013.01)

(58) Field of Classification Search
CPC .......... A61B 2018/00589; A61B 2018/00595; A61B 2018/0063; A61B 2018/00642; A61B 2018/00702; A61B 2018/00791; A61B 2018/00875
See application file for complete search history.

(56) References Cited

FOREIGN PATENT DOCUMENTS

| JP | 2006-288430 | 10/2006 |
|---|---|---|
| JP | 2009-247893 A | 10/2009 |

OTHER PUBLICATIONS

May 14, 2019 Office Action issued in Japanese Patent Application No. 2017-557534.
Mar. 8, 2016 International Search Report issued in International Patent Application PCT/JP2015/085674.
Mar. 8, 2016 Written Opinion issued in International Patent Application PCT/JP2015/085674.
Jul. 18, 2019 Extended Search Report issued in Europian Patent Application No. 15911270.5.
May 19, 2020 Office Action issued in Chinese Patent Application No. 201580085398.6.
Jan. 31, 2012 Simulated electronic technology basics. pp. 221-224.
Aug. 31, 2007 Microcomputer relay protection basics. pp. 87-92.
May 31, 2008 Circuit Analysis training course. p. 108.

* cited by examiner

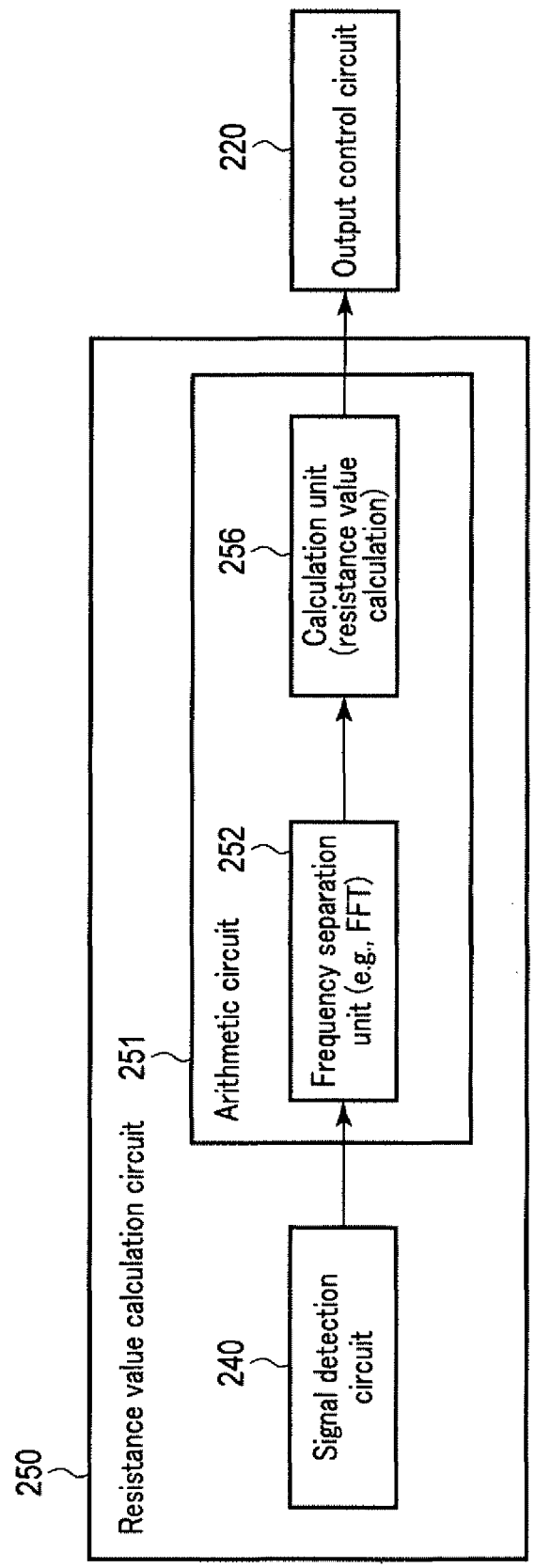
F I G. 9

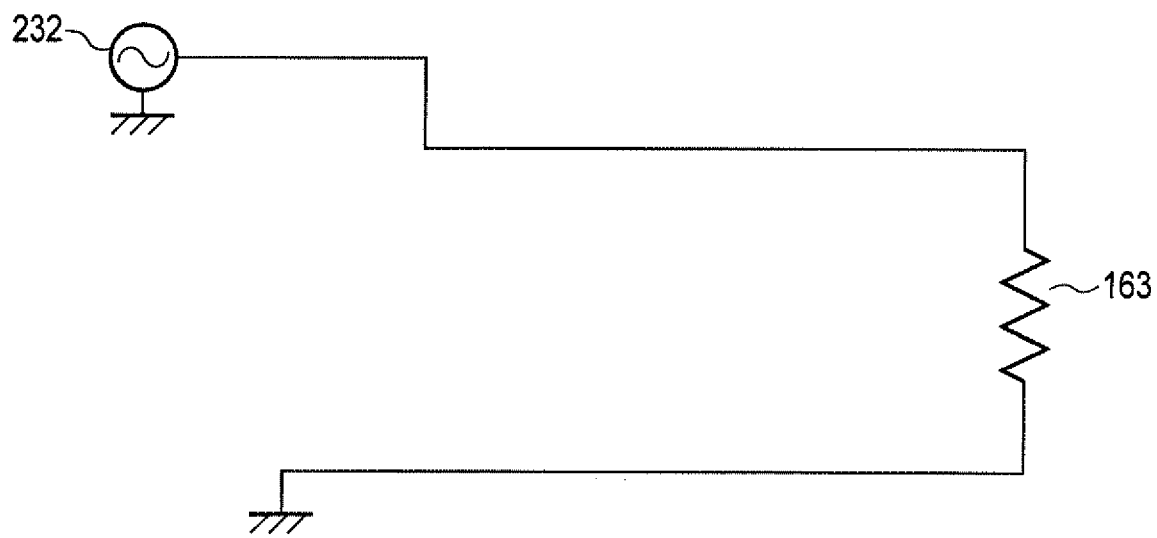
F I G. 12
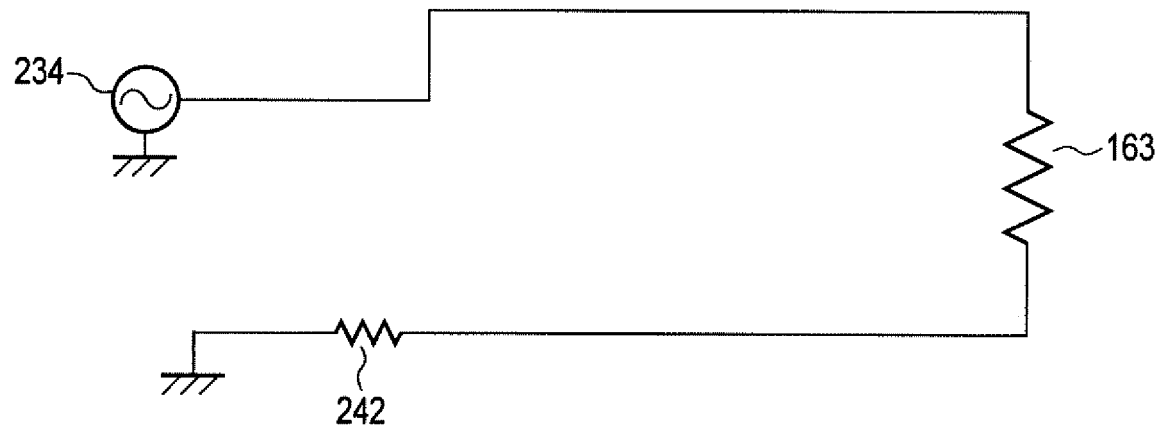
F I G. 13

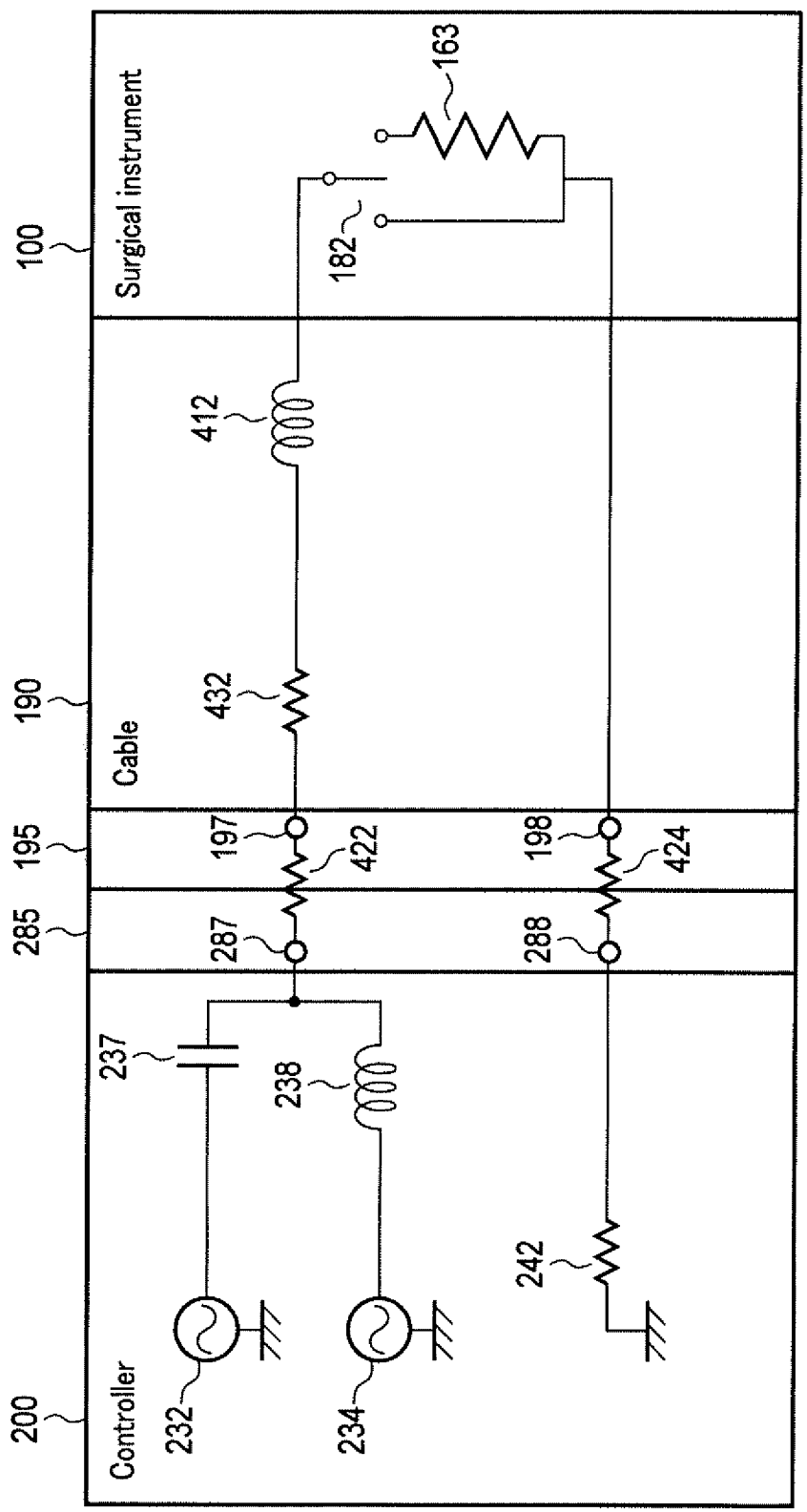
F I G. 15

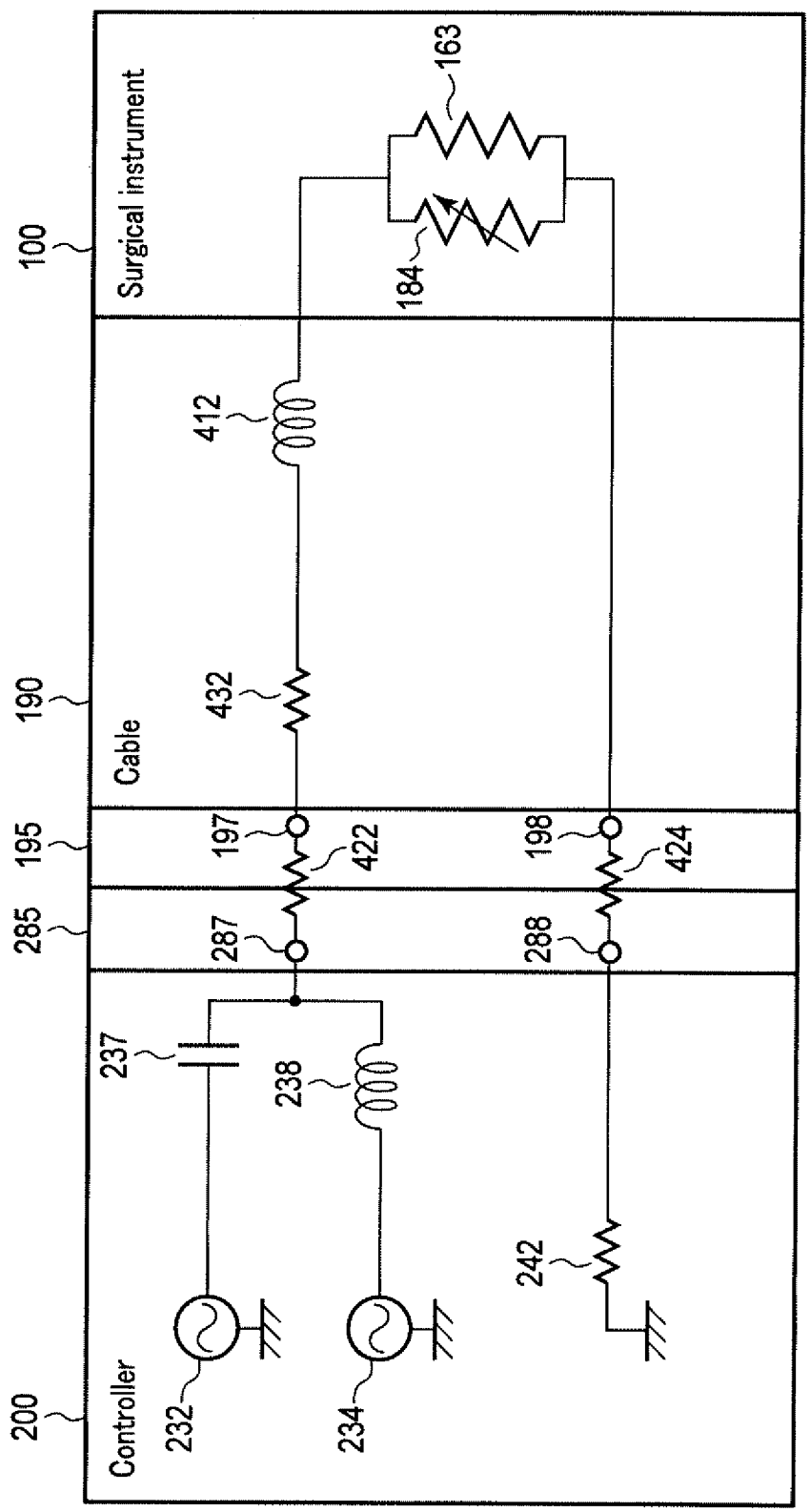
F I G. 16

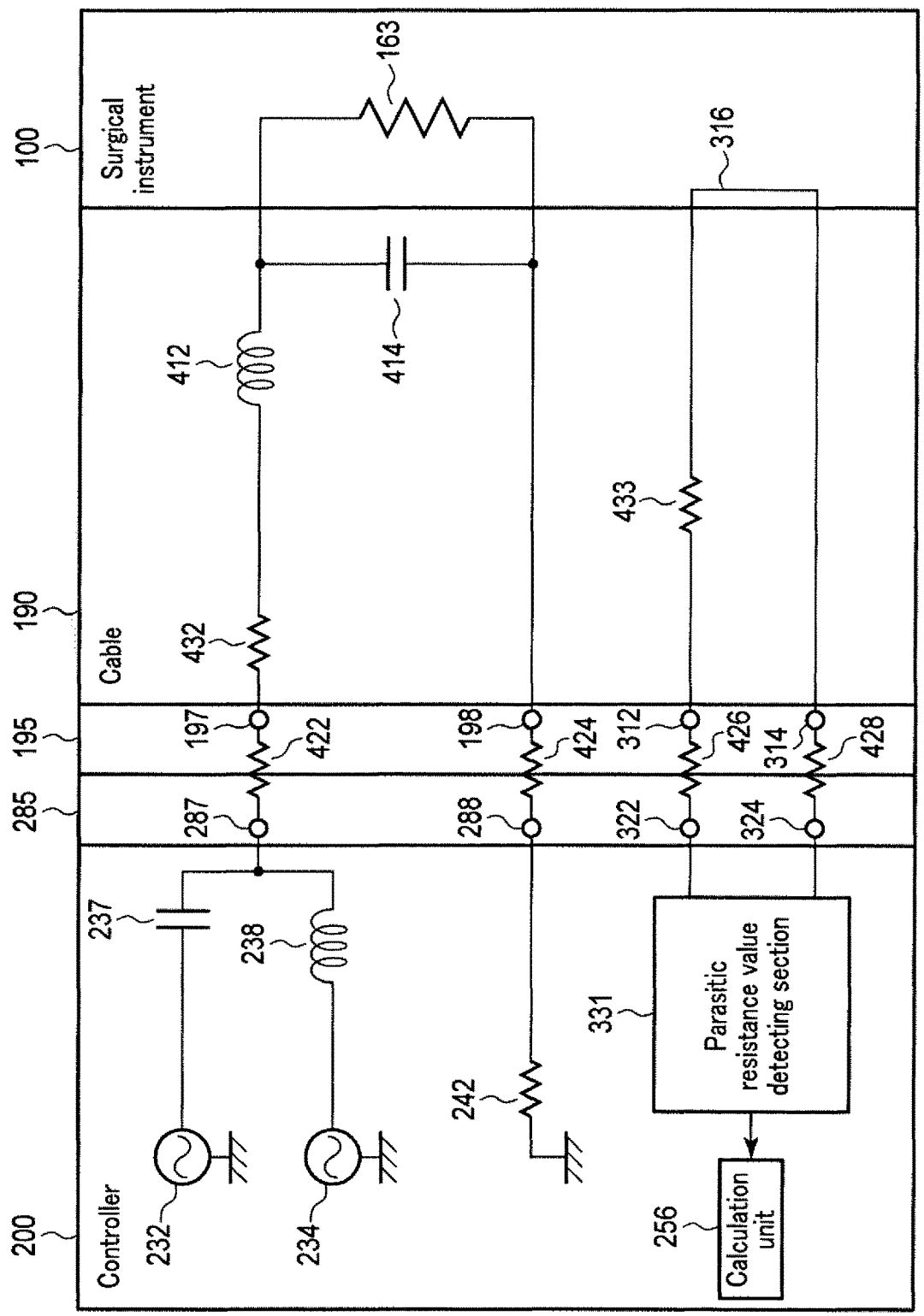
F I G. 18

CONTROL DEVICE FOR SURGICAL INSTRUMENT, AND SURGICAL SYSTEM

CROSS-REFERENCE TO RELATED APPLICATIONS

This application is a Continuation Application of PCT Application No. PCT/JP2015/085674, filed Dec. 21, 2015, the entire contents of which are incorporated herein by reference.

BACKGROUND OF THE INVENTION

1. Field of the Invention

The present invention relates to a control device for a surgical instrument, and a surgical system.

2. Description of the Related Art

Surgical instruments are known in which a living tissue as a treatment target portion is held by a holding section equipped with a heater and the living tissue is treated with heat generated by the heater.

For example, Jpn. Pat. Appln. KOKAI Publication No. 2009-247893 discloses a surgical instrument capable of applying a high-frequency voltage to a living tissue held by a holding section and capable of applying heat generated by a heater to the living tissue. In this surgical instrument, the impedance information and the phase information on the living tissue are acquired via an electrode for applying a high-frequency voltage to the living tissue, and the output of the heater is controlled based on the acquired information.

Also, Jpn. Pat. Appln. KOKAI Publication No. 2009-247893 discloses that the temperature of the heater is determined based on the electric resistance value of the heater having temperature dependency. This surgical instrument acquires the heater temperature based on the electric resistance value of the heater and controls the temperature of the heater based on the acquired heater temperature.

BRIEF SUMMARY OF THE INVENTION

According to one aspect of the present invention, a control device controls a surgical instrument including a heater. The control device includes a first power supply, a second power supply, a resistance value calculation section, and an output control circuit. The first power supply outputs a first current having a first frequency and supplied to the heater. The second power supply outputs a second current combined with the first current, supplied to the heater and having a second frequency different from the first frequency. The resistance value calculation section separates a signal component related to the second current from the first and second currents having passed through the heater, and calculates a heater resistance value based on the signal component. The output control circuit controls a temperature of the heater based on the heater resistance value.

According to one aspect of the present invention, a surgical system includes the above-mentioned control device and a surgical instrument including a heater configured to generate heat when supplied with power from the control device.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 1 is a diagram showing an example of how a surgical system according to one embodiment looks like.

FIG. 9 is a block diagram schematically showing a configuration example of a resistance value calculation section according to the second example.

FIG. 12 is a diagram schematically showing an example of an equivalent circuit of a first power supply according to the second modification of the first embodiment.

FIG. 13 is a diagram schematically showing an example of an equivalent circuit of a second power supply according to the second modification of the first embodiment.

FIG. 15 is a diagram schematically showing a configuration example of a surgical system according to the third embodiment.

FIG. 16 is a diagram schematically showing a configuration example of a surgical system according to the first modification of the third embodiment.

FIG. 18 is a diagram schematically showing a configuration example of a surgical system according to the fourth embodiment.

DETAILED DESCRIPTION OF THE INVENTION

First Embodiment

Figure 1:
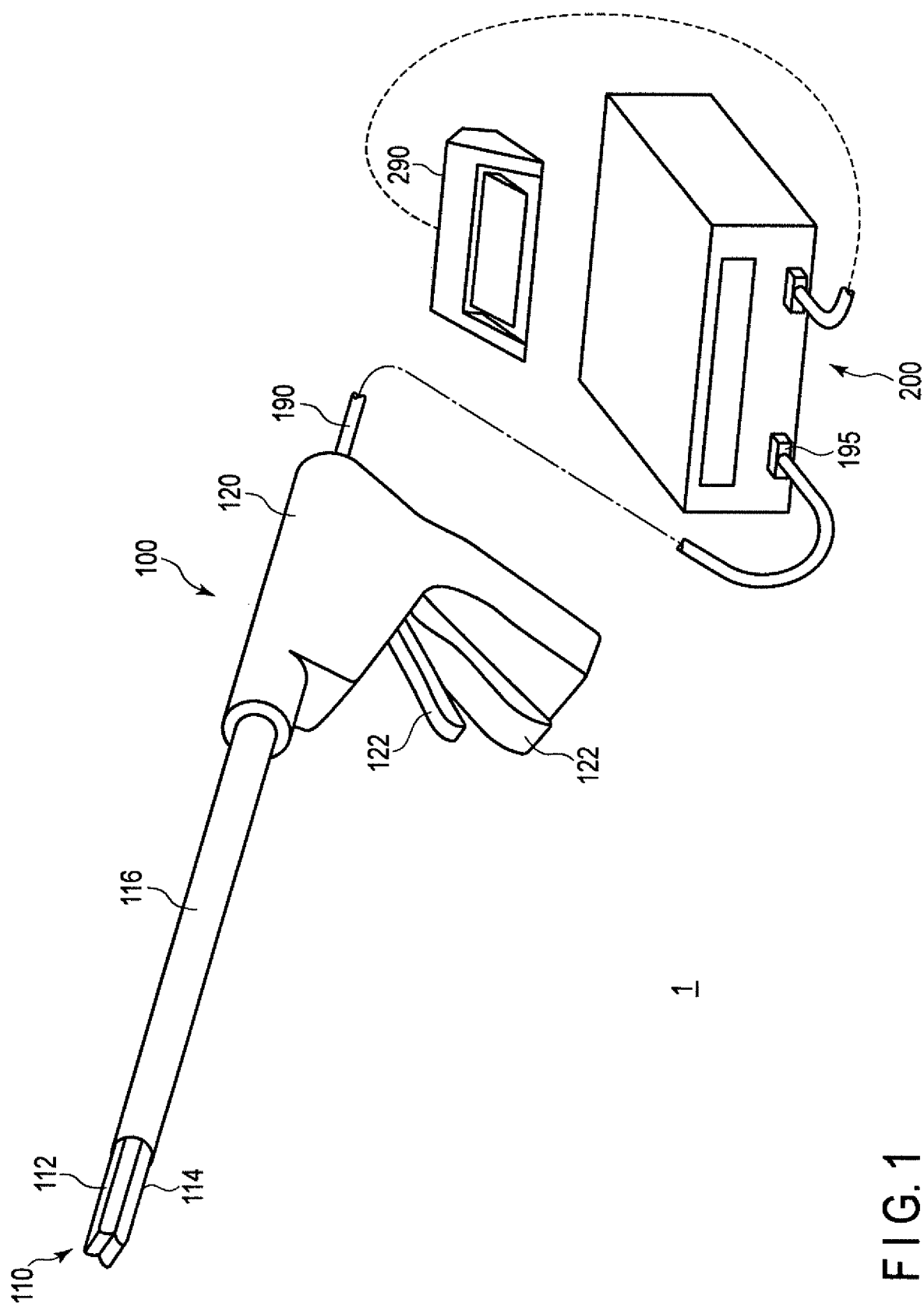

A description will now be given of the first embodiment with reference to the accompanying drawings. FIG. 1 schematically illustrates how the surgical system 1 of the present embodiment looks like. The surgical system 1 is an apparatus used for treating a living tissue. For example, it is used for a treatment including tissue sealing, hemostasis, coagulation, tissue dissection or incision. The surgical system 1 performs treatment by applying energy to the living tissue.
<Configuration of Surgical System>

As shown in FIG. 1, the surgical system 1 includes a surgical instrument 100 for performing a treatment and a controller 200 for supplying power to the surgical instrument 100. In the surgical system 1, the surgical instrument 100 and the controller 200 operate in cooperation.

The surgical instrument 100 is, for example, a surgical instrument for surgical treatments of penetrating an abdominal wall. The surgical instrument 100 includes a handle 120, a shaft 116 attached to the handle 120, and a holding section 110 that is an end effector provided at the distal end of the shaft 116.

The holding section 110 has a first holding member 112 and a second holding member 114. The first holding member 112 is displaced with respect to the second holding member 114, so that the holding section 110 opens and closes. The holding section 110 is configured to grasp a living tissue, which is a treatment target, between the first holding member 112 and the second holding member 114. The holding section 110 is a treatment part that holds the living tissue as the treatment target, and performs treatment such as coagulation or incision of the living tissue. The handle 120 includes a plurality of operation knobs 122 for operating the holding section 110.

In the descriptions set forth below, a portion of the surgical instrument 100 that is closer to the holding section 110 will be referred to as a distal side, and a portion that is closer to the handle 120 will be referred to as a proximal side.

It should be noted that the shape of the surgical instrument 100 shown in the drawings is nothing but an example, and other shapes may be used as long as they have similar functions. For example, the length and shape of the shaft can be changed as appropriate. The technique according to the present embodiment is not limited to a treatment device for rigid endoscopic surgery, such as that shown in FIG. 1, but is also applicable to a treatment device used for endoscopic surgery using a flexible endoscope.

The surgical instrument 100 is connected to the controller 200 through a cable 190. The cable 190 and the controller 200 are connected by a cable connector 195, and they are detachable from each other. That is, the surgical system 1 is configured such that a surgical instrument 100 to be used for each treatment can be properly chosen.

A foot switch 290 is connected to the controller 200. The foot switch 290 operated by foot may be replaced with a manually operable hand switch or any other type of switch. The supply of energy to the surgical instrument 100 from the controller 200 is switched on or off by operating the pedal of the foot switch 290 by an operator.

A heater for converting power into heat is provided near that portion of at least one of the first and second holding members 112 and 114 which comes into contact with a living tissue. Heat generated by the heater is transmitted to the living tissue. The living tissue is treated with the heat.

Figure 2:
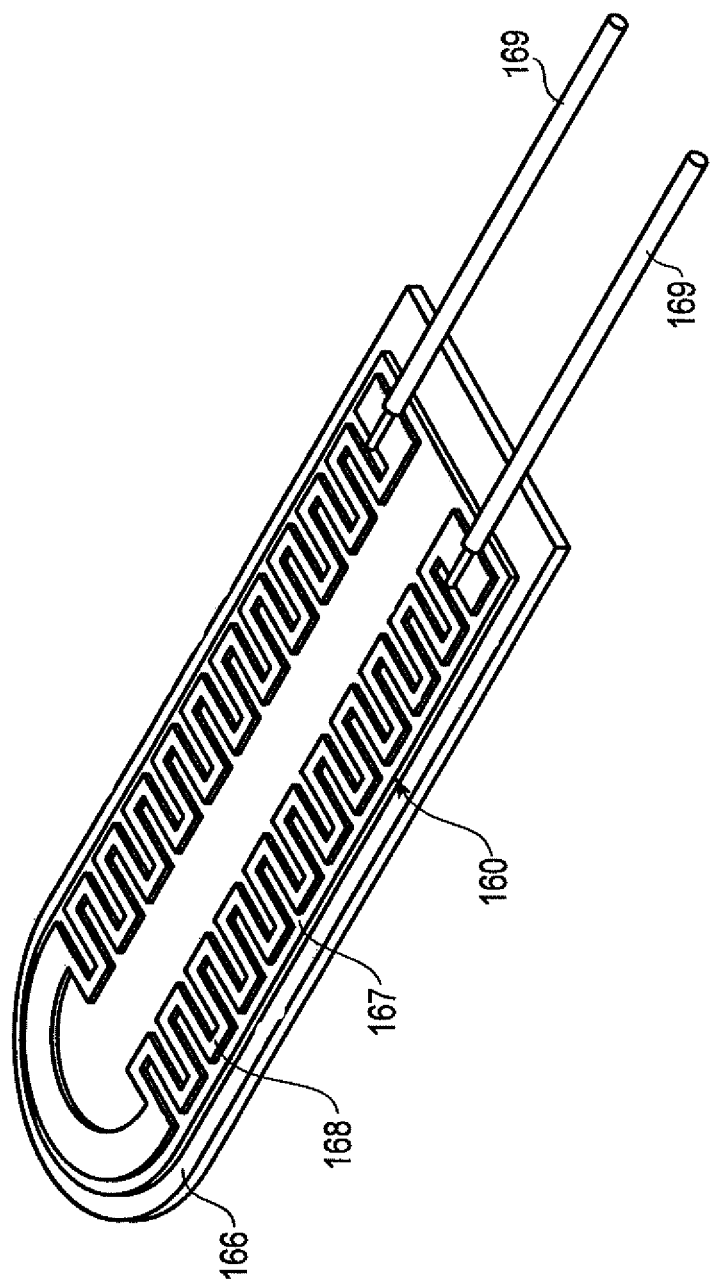
FIG. 2 is a diagram schematically showing a configuration example of a heater and its neighboring portions according to one embodiment.

The heater 160 and its neighboring structure will be described with reference to FIG. 2. A heat transfer member 166 made of, for example, copper is provided on those surfaces of the first and second holding members 112 and 114 which come into contact with a living tissue. The heater 160 has a structure in which a heat generating member 168 is provided on a substrate 167. The substrate 167 is, for example, a polyimide substrate. The substrate 167 is slightly smaller than the heat transfer member 166 and has the same shape as the heat transfer member 166. The heat generating member 168 is, for example, a resistive pattern of stainless steel (SUS) formed on the substrate 167. Both ends of the heat generating member 168 are provided on the proximal end side, and the heat generating member 168 has a substantially U-shaped pattern. This pattern is formed to have a small line width in order to increase electrical resistance and have a corrugated shape in order to cover a wide range of the substrate. One end of a conductive wire 169 is connected to each of the ends of the heat generating member 168.

The other end of each conductive wire 169 is electrically connected to the power supply device 230 of the controller 200 to be described later. When power is supplied to the heat generating member 168, the heat generating member 168 converts the power into heat and thus generates heat. The heat generated by the heat generating member 168 is transmitted to the heat transfer member 166 via the substrate 167. This heat is transmitted to the living tissue that is in contact with the heat transfer member 166, and the living tissue is subjected to heat treatment.

In the surgical system 1 according to the present embodiment, the temperature of the heat transfer member 166 is controlled by the controller 200. It should be noted here that the temperature of the heat transfer member 166 is controlled by feedback control that is performed with the temperature of the heater 160 acquired. Since a known predetermined relationship exists between the resistance value of the heat generating member 168 and the temperature thereof, the temperature of the heater 160 is calculated based on the resistance value of the heat generating member 168. That is, the controller 200 acquires the resistance value of the heat generating member 168 and calculates the temperature of the heat generating member 168 based on this resistance value and the known predetermined relationship.

Figure 3:
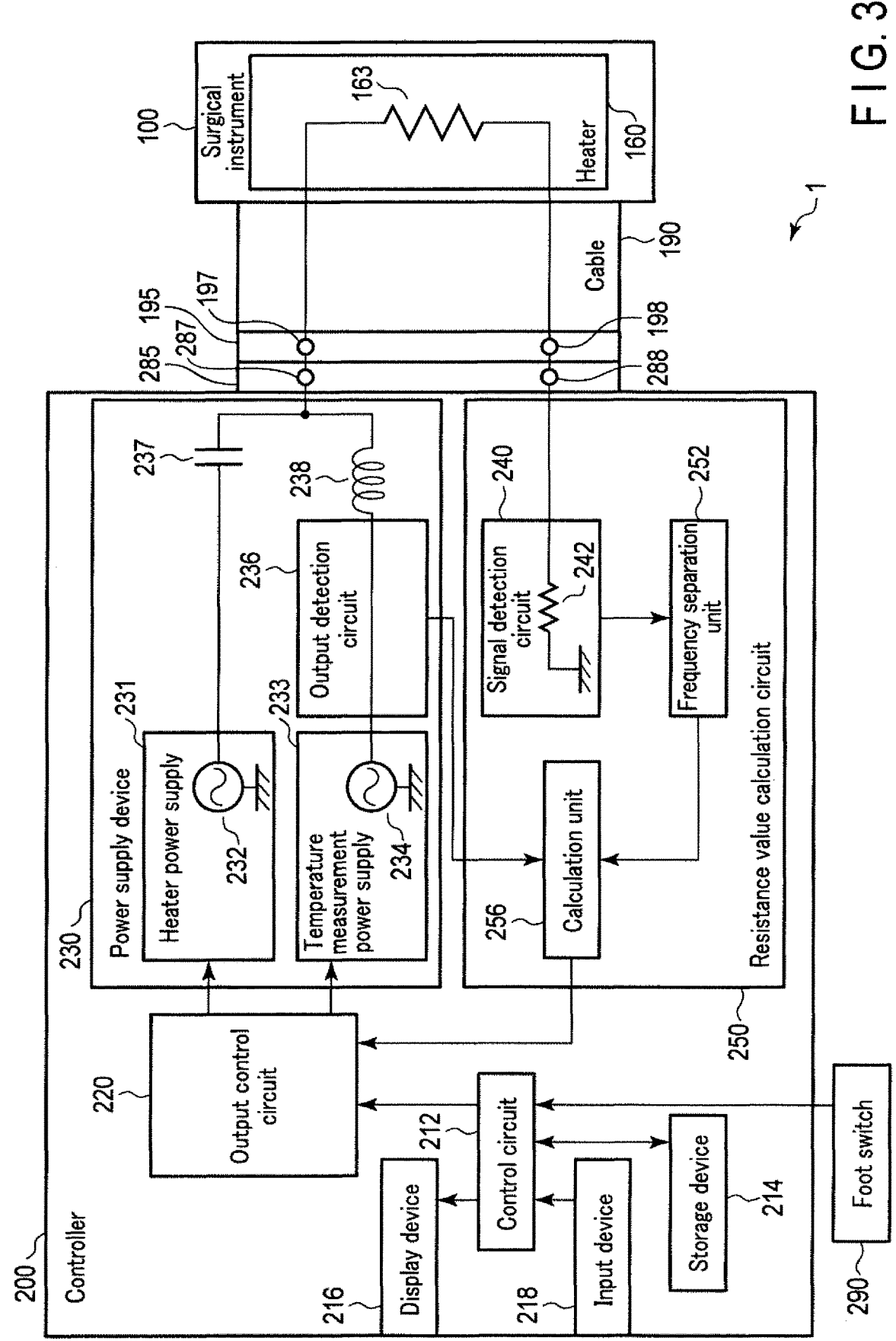
FIG. 3 is a block diagram schematically illustrating a configuration example of a surgical system according to one embodiment.

FIG. 3 schematically illustrates a configuration example of the surgical system 1. The surgical instrument 100 is provided with the heater 160, as described above. The heater 160 has a heater resistor 163 electrically corresponding to the heat generating member 168. One end of the heater resistor 163 is connected to the first terminal 197 of the cable connector 195 via the cable 190. The other end of the heater resistor 163 is connected to the second terminal 198 of the cable connector 195 via the cable 190.

The controller 200 comprises a control circuit 212, a storage device 214, a display device 216, an input device 218, an output control circuit 220, a power supply device 230, a resistance value calculation circuit 250, and a power supply device connector 285.

The power supply device connector 285 is a terminal to which the cable connector 195 is connected. The power supply device connector 285 has a third terminal 287 connected to the first terminal 197 of the cable connector 195 and a fourth terminal 288 connected to the second terminal 198 of the cable connector 195.

The power supply device 230 includes two power supplies, namely, a heater power supply 231 and a temperature measurement power supply 233. The heater power supply 231 includes a first power supply 232 which is, for example, an AC power supply. On the other hand, the temperature measurement power supply 233 includes a second power supply 234 which is, for example, an AC power supply. The heater power supply 231 is a power supply for outputting power for heating the heater 160. On the other hand, the temperature measurement power supply 233 is a power supply that outputs power for the purpose of measuring the resistance value of the heater 160 in order to acquire the temperature of the heater 160.

The output of the heater power supply 231 varies in accordance with the amount of heat to be supplied, that is, in accordance with the difference between the current temperature of the heater 160 and the target temperature. The output of the temperature measurement power supply 233 is a predetermined constant voltage, current or power. In general, the first output that is the output of the heater power supply 231 is higher than the second output that is the output of the temperature measurement power supply 233. For example, the current value of the second current related to the second output is smaller than the current value of the first current related to the first output. In the present embodiment, the first frequency that is the output frequency of the first power supply 232 of the heater power supply 231 is higher than the second frequency that is the output frequency of the second power supply 234 of the temperature measurement power supply 233. Since, as will be described later, the first frequency and the second frequency are separated, the first frequency is preferably 10 times or more the second frequency in order to facilitate separation. For example, the first frequency is 100 kHz, and the second frequency is 10 kHz.

One end of the first power supply 232 is grounded, and the other output end is connected to the third terminal 287 via a first capacitor 237. One end of the second power supply 234 is grounded, and the other output end is connected to the third terminal 287 via an output detection circuit 236 and a first inductor 238. The output detection circuit 236 is a circuit for detecting the output voltage of the second power supply 234. The output detection circuit 236 transmits the detected output voltage to the calculation unit 256 of the resistance value calculation circuit 250 to be described later.

In general, a capacitor passes high-frequency signals and an inductor passes low-frequency signals. Therefore, an output signal of the heater power supply 231 having the first frequency, which is a comparatively high frequency, passes through the first capacitor 237. An output signal of the temperature measurement power supply 233 having the second frequency, which is a comparatively low frequency, passes through the first inductor 238. In this way, the first capacitor 237 and the first inductor 238 serve to suppress mutual interference between the output of the heater power supply 231 and the output of the temperature measurement power supply 233. Thus, the first current output from the first power supply 232 and the second current output from the second power supply 234 are combined and flow through the same path.

The resistance value calculation circuit 250 includes a signal detection circuit 240, a frequency separation unit 252 and a calculation unit 256. The signal detection circuit 240 detects a signal for calculating the resistance value of the heater resistor 163 of the surgical instrument 100. More specifically, the signal detection circuit 240 includes a sensing resistor 242 connected in series with the heater resistor 163. One end of the sensing resistor 242 is connected to the heater resistor 163, and the other end thereof is grounded. The signal detection circuit 240 detects a potential difference across the sensing resistor 242, that is, a voltage applied across the sensing resistor 242, as a detection voltage.

The frequency separation unit 252 extracts a component having a second frequency from the detection voltage detected by the signal detection circuit 240. The calculation unit 256 calculates a resistance value of the heater resistor 163, based on the detection voltage having the second frequency extracted by the frequency separation unit 252 and the output voltage detected by the output detection circuit 236.

There are several configurations of the frequency separation unit 252, as will be described in detail later. The frequency separation unit 252 may be, for example, a filter circuit. That is, the frequency separation unit 252 may be constituted by a low-pass filter that passes only signals of the comparatively low second frequency of the temperature measurement power supply 233. Alternatively, the frequency separation unit 252 may be constituted by an arithmetic circuit. This type of frequency separation unit 252 performs such arithmetic operations as fast Fourier transform (FFT) or wavelet transform. By such arithmetic operations, the frequency separation unit 252 may extract only signals of comparatively a low second frequency derived from the temperature measurement power supply 233.

The output control circuit 220 controls the operations of the heater power supply 231 and the temperature measurement power supply 233, based on the resistance value of the heater resistor 163 calculated by the calculation unit 256 and the command acquired from the control circuit 212. This control includes temperature control of the heater 160 so that appropriate treatments can be taken.

The control circuit 212 controls the operation of each portion of the controller 200. The display device 216 includes, for example, a liquid crystal display panel, an LED lamp, and the like. Under the control of the control circuit 212, the display device 216 presents various information on the surgical system 1 to the user. The input device 218 includes general input devices, such as a keyboard, a touch panel and a switch. The input device 218 acquires an input from the user and transmits it to the control circuit 212. Further, an input to the foot switch 290 is transmitted to the control circuit 212. The control circuit 212 transmits, to the output control circuit 220, various kinds of information, for example, information on an output setting value of the surgical instrument 100 and information indicating that the foot switch is on or off. The storage device 214 stores programs related to the control of the control circuit 212, various necessary parameters, and the like.

The control circuit 212, the output control circuit 220 and the calculation unit 256 include an integrated circuit, such as a Central Processing Unit (CPU), an Application Specific Integrated Circuit (ASIC), or a Field Programmable Gate Array (FPGA). The control circuit 212, the output control circuit 220, and the calculation unit 256 may each be constituted by one integrated circuit or the like, or a combination of a plurality of integrated circuits. In addition, two or more of the control circuit 212, the output control circuit 220, the calculation unit 256 and the like may be constituted by one integrated circuit. The operations of these integrated circuits are performed in accordance with a program recorded in the storage device 214 or in a recording area of an integrated circuit.

<Calculation Method of Heater Resistance Value>

Figure 4:
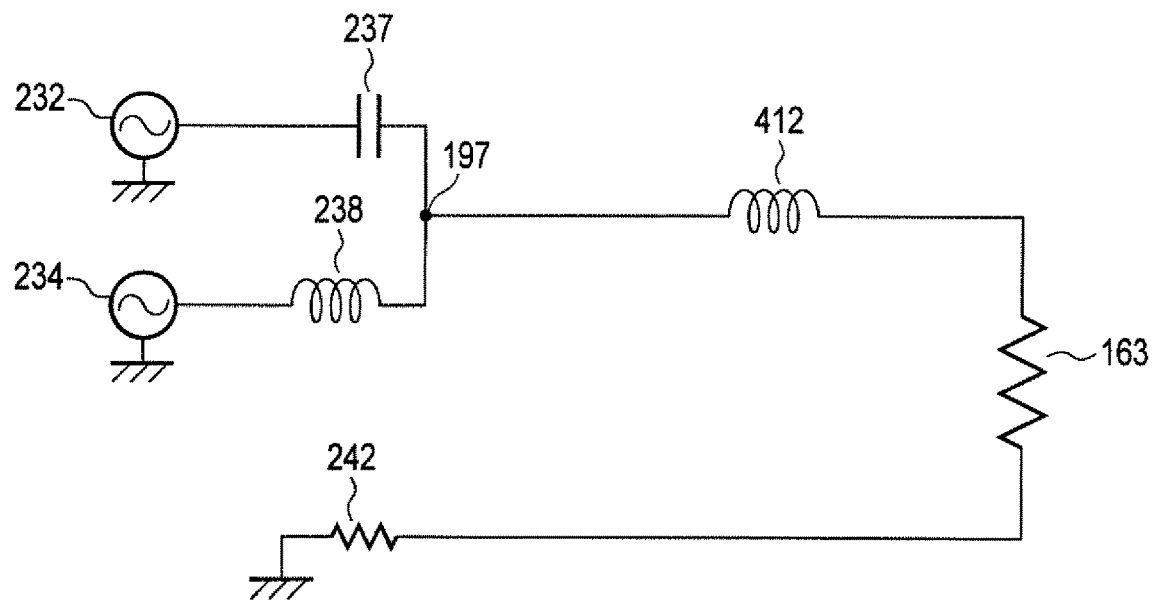
FIG. 4 is a diagram schematically showing an electric circuit of the heater of the surgical system of the first embodiment.

In the surgical system 1 according to the present embodiment, a parasitic component attributable mainly to the cable 190 is present. FIG. 4 shows a circuit diagram including the parasitic component of the surgical system 1 of the present embodiment. As shown in FIG. 4, a second inductor 412 is present as the parasitic component between the first terminal 197 and the heater resistor 163. Therefore, the phases of the output voltages of the first and second power supplies 232 and 234 are inevitably shifted from the phase of the voltage detected by the signal detection circuit 240. In the present embodiment, this phase shift is adjusted.

Figure 5:
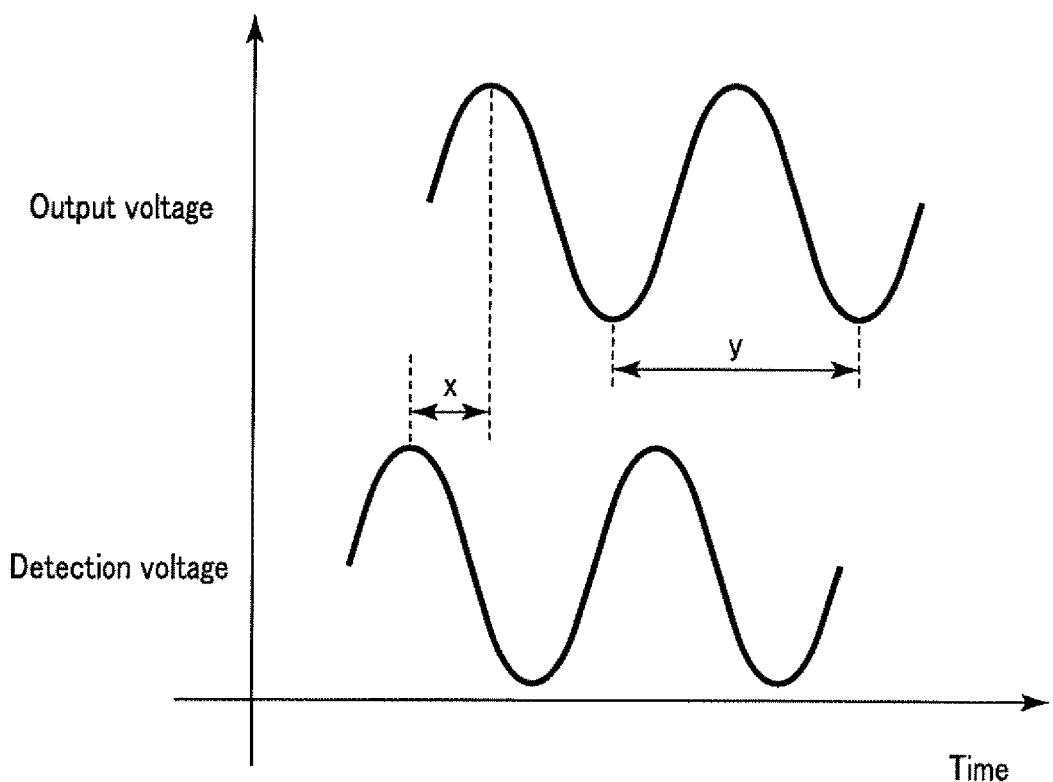
FIG. 5 is a diagram for illustrating the phase difference between an output voltage and a detection voltage.

FIG. 5 shows an example of the waveforms of an output voltage detected by the output detection circuit 236 and a detection voltage detected by the signal detection circuit 240. In this Figure, x indicates a phase shift and y indicates one cycle. A phase difference α is calculated as below, using x and y, $$\alpha = (x/y) \times 360 [\deg]$$

With respect to the detection voltage Vdet detected by the signal detection circuit 240, a correction detection voltage Vdet_c, which is obtained by correcting the phase difference α, is expressed by:

$$V\text{det}\_c = V\text{det} \times \cos(\alpha)[V]$$

In this way, unnecessary phase information included in the signal detected by the signal detection circuit 240 is removed.

Since the heater resistor 163 and the sensing resistor 242 whose resistance value is known are connected in series, a correction detection voltage Vdet_c is expressed by $$V\text{det}\_c = (R\text{det}/(R\text{det} + R\text{heat})) \times V\text{out}$$

where Rheat is a heater resistor 163, Rdet is a sensing resistor, and Vout is an output voltage. Therefore, the heater resistance Rheat is expressed by $$R\text{heat} = R\text{det}(V\text{out} - V\text{det}\_c)/V\text{det}\_c$$

<Operation of Surgical System>

A description will now be given of an operation performed by the surgical system 1 of the present embodiment. First, the operator operates the input device 218 of the controller 200 to enter output conditions of the surgical system 1, including a target temperature and a heating time of the treatment. The output conditions may be entered by individually setting a value for each parameter or by selecting a set of setting values suitable to the treatment.

The handle 120 and the shaft 116 of the surgical instrument 100 are inserted, for example, into an abdominal cavity through an abdominal wall. The operator operates the operation knobs 122 to open or close the holding section 110, and holds a living tissue as a treatment target with the first holding member 112 and the second holding member 114. At this time, the living tissue to be treated comes into contact with the heat transfer members 166 provided on the first and second holding members 112 and 114.

The operator operates the foot switch 290 after holding the living tissue to be treated with the holding section 110. When the foot switch 290 is turned on, power is supplied from the controller 200 to the heater 160 via a conductive wire passing through the cable 190. The target temperature is, for example, 200° C. At this time, current flows through the heat generating members 168. The heat generating members 168 generate heat because of this current. The heat generated by the heat generating members 168 is transmitted to the heat transfer members 166 via the substrates 167. As a result, the temperature of the heat transfer members 166 increases.

Figure 6:
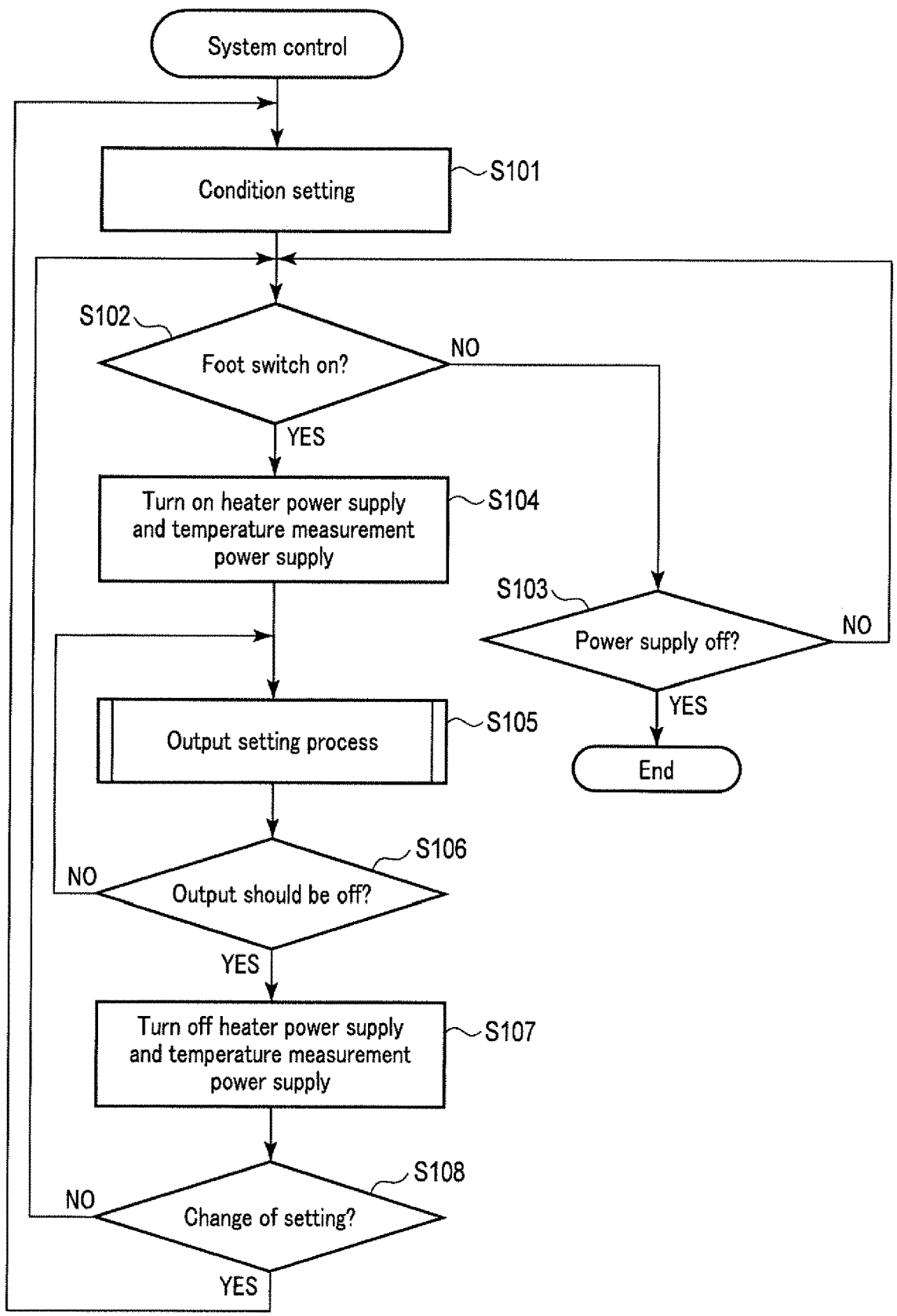
FIG. 6 is a flowchart illustrating an example of a system control method according to one embodiment.

By the heat transmitted to the heat transfer members 166, the living tissue that is in contact with the heat transfer members 166 is cauterized and coagulated. When the living tissue is coagulated by heating, the supply of power to the heater 160 is stopped. In this manner, the treatment of the living tissue is completed How the controller 200 performs a system control process in the above operation will be described, referring to the flowchart shown in FIG. 6.

In step S101, the controller 200 performs condition setting. That is, the control circuit 212 causes the display device 216 to display for presenting the user a message prompting the user to enter conditions of the treatment, such as a target temperature and a heating time. Alternatively, the control circuit 212 causes the display device 216 to display currently-set conditions of the procedure, such as a target temperature and a heating time. The control circuit 212 acquires user's inputs from the input device 218. The control circuit 212 sets conditions of the treatment, such as a target temperature and a heating time, in accordance with the user's inputs obtained from the input device 218. The control circuit 212 transmits the set conditions to the output control circuit 220.

In step S102, the control circuit 212 determines whether or not the foot switch 290 is on. If the foot switch 290 is not on, the process proceeds to step S103. In step S103, it is determined whether or not the power supply is turned off. Unless the power supply is turned off, the process returns to step S102. That is, while the foot switch 290 is off and the power supply is on, the process repeats steps S102 and S103 and stands by. When the power supply is turned off, the system control process ends. In step S102, if the foot switch 290 is on, the process proceeds to step S104.

In step S104, the controller 200 turns on the output of the heater power supply 231 and the temperature measurement power supply 233. That is, the control circuit 212 informs the output control circuit 220 that the foot switch 290 is turned on. At this time, the output control circuit 220 controls the operations of the heater power supply 231 and the temperature measurement power supply 233 such that these power supplies output power. The output of the heater power supply 231 is an AC voltage having a first frequency, and the voltage value is a predetermined initial value. The output of the temperature measurement power supply 233 is an AC voltage having a second frequency, and the voltage value is a predetermined measurement voltage value.

Figure 7:
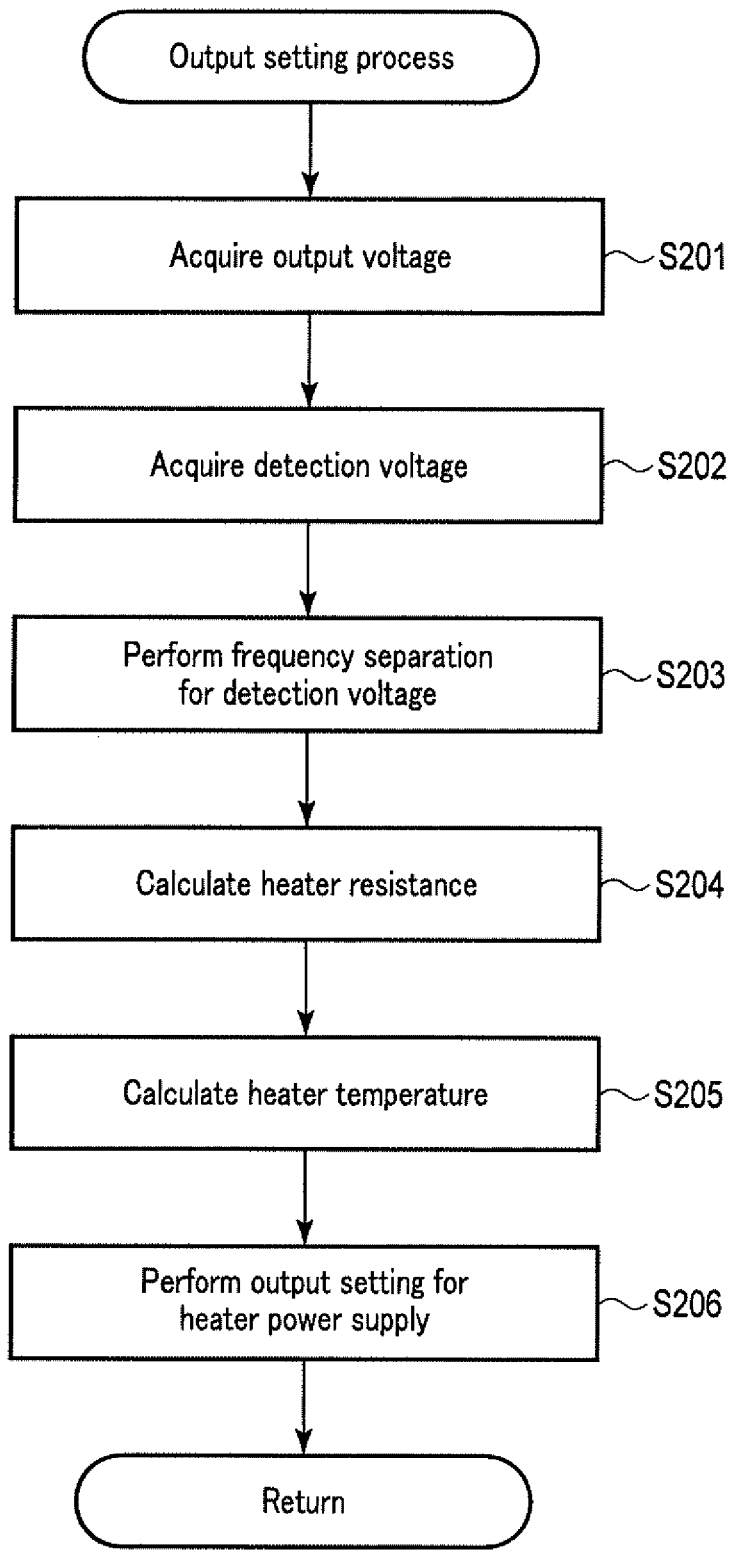
FIG. 7 is a flowchart showing an example of an output setting process according to one embodiment.

In step S105, the controller 200 performs an output setting process. The output setting process will be described with reference to the flowchart shown in FIG. 7.

In step S201, the calculation unit 256 of the resistance value calculation circuit 250 acquires an output voltage Vout of the temperature measurement power supply 233 from the output detection circuit 236.

In step S202, the resistance value calculation circuit 250 acquires a detection signal related to the detection voltage Vdet from the signal detection circuit 240.

In step S203, the frequency separation unit 252 of the resistance value calculation circuit 250 acquires a detection voltage Vdet, which is a signal component made to have a second frequency by frequency separation, from the detection signal of the signal detection circuit 240. The detection voltage Vdet is transmitted to the calculation unit 256.

In step S204, the calculation unit 256 calculates a heater resistance Rheat according to the above calculation method, based on the output voltage Vout and the detection voltage Vdet. The calculation unit 256 transmits the calculated heater resistance Rheat to the output control circuit 220.

In step S205, the output control circuit 220 calculates a heater temperature indicative of the temperature of the heater 160, based on the heater resistance Rheat. The heater temperature is obtained, for example, based on a table stored in the storage device 214 and showing the relationship between the heater resistance Rheat and the heater temperature. The heater temperature may be calculated by the calculation unit 256.

In step S206, the output control circuit 220 performs output setting for the heater power supply 231, using the heater temperature. For example, the output control circuit 220 increases or decreases the output voltage of the heater power supply 231, based on the difference between the target temperature set in step S101 and the heater temperature.

In the above manner, the output setting process is completed. The process proceeds to step S106 of the system control process described with reference to FIG. 6.

In step S106, the control circuit 212 determines whether or not to turn off the output. For example, if the foot switch 290 is turned off, it is determined that the output should be turned off. Alternatively, if the time elapsed from the time when the output is turned on exceeds a predetermined period, it is determined that the output should be turned off. Unless it is determined that the output should be turned off, the process returns to step S105. That is, the output is continued, and the output of the heater power supply 231 is adjusted again. On the other hand, if it is determined that the output should be turned off, the process proceeds to step S107.

In step S107, the controller 200 turns off the output of the heater power supply 231 and the temperature measurement power supply 233.

In step S108, it is determined whether or not change of the condition setting made in S101 is requested. If the change of the condition setting is requested, the process returns to step S101. In other words, condition setting is performed again, and the output is started when the foot switch 290 is turned on. Unless the change of the condition setting is requested, the process returns to step S102. That is, when the foot switch 290 is turned on, the output performed again.

<Configuration of Resistance Value Calculation Section>

The configuration of the resistance value calculation circuit 250 will be described. A signal having the second frequency derived from the signal output from the temperature measurement power supply 233 can be extracted from the detection signal acquired by the signal detection circuit 240 in a number of methods. Examples of the methods will be described.

(First Method)

Figure 8:
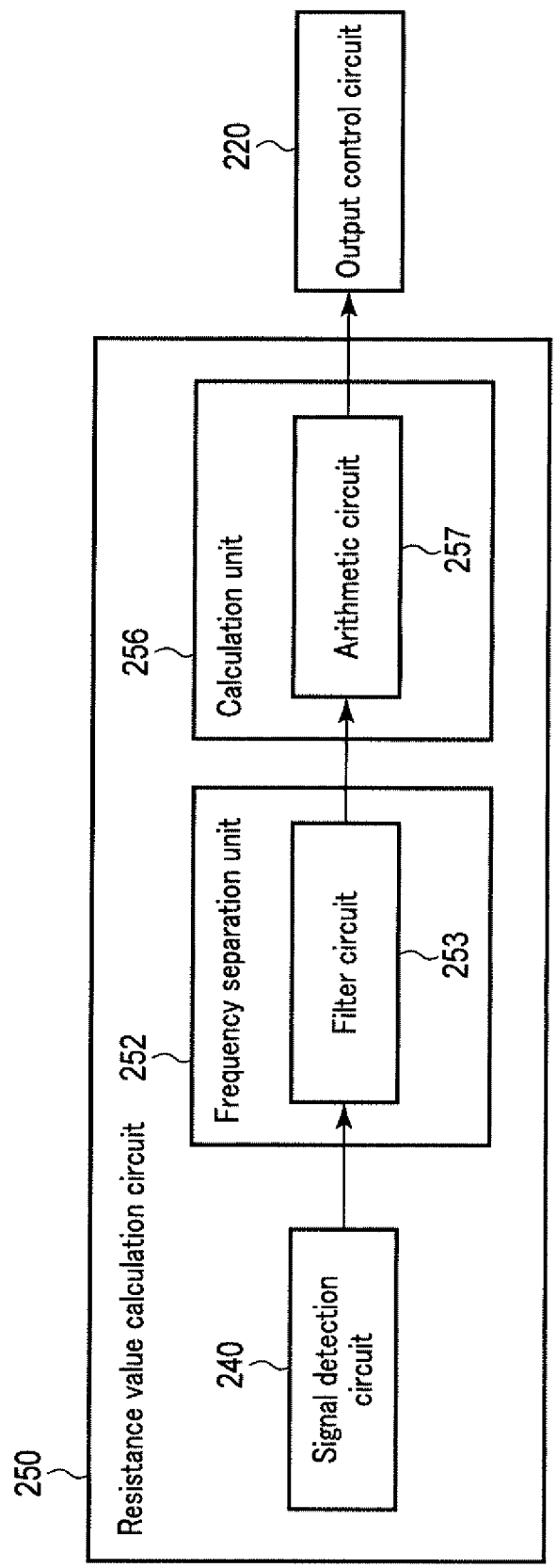
FIG. 8 is a block diagram schematically showing a configuration example of a resistance value calculation section according to the first example.

The first method is a method using a filter circuit. FIG. 8 schematically shows a configuration example of the resistance value calculation circuit 250 that employs the filter circuit. In this example, the frequency separation unit 252 includes a filter circuit 253. The calculation unit 256 includes an arithmetic circuit 257. In the present embodiment, the filter circuit 253 includes a low-pass filter because the second frequency is lower than the first frequency. Of the signals detected by the signal detection circuit 240, a signal passing through the filter circuit 253 is input to the arithmetic circuit 257. That is, of the signals detected by the signal detection circuit 240, a signal derived from the signal output from the temperature measurement power supply 233 and having the second frequency is input to the arithmetic circuit 257. In this way, the arithmetic circuit 257 acquires a detection voltage Vdet. The arithmetic circuit 257 calculates a heater resistance Rheat using the detection voltage Vdet. The calculated heater resistance Rheat is transmitted to the output control circuit 220.

(Second Method)

The second method is a method in which frequency separation is performed by an arithmetic operation. FIG. 9 schematically shows a configuration example of the resistance value calculation circuit 250 that performs frequency separation by an arithmetic operation. The resistance value calculation circuit 250 according to the second method includes an arithmetic circuit 251. In the arithmetic circuit 251, an arithmetic operation for frequency separation, such as fast Fourier transform or wavelet transform, is performed by a frequency separation unit 252. A signal corresponding to the second frequency included in the frequencies obtained by the operation is extracted. In the arithmetic circuit 251, a heater resistance Rheat is calculated by the calculation unit 256. The calculated heater resistance Rheat is transmitted to the output control circuit 220.

<Advantages of Present Embodiment>

According to the present embodiment, a heater resistance Rheat can be accurately obtained. To obtain the heater resistance Rheat, it is also possible to use the output of the heater power supply 231 for causing the heater 160 to generate heat. However, the output of the heater power supply 231 changes in accordance with the target temperature and the current temperature of the heater 160. In order to obtain the heater resistance Rheat based on the output that changes in this manner, for example, the signal detection circuit 240 is required to accurately detect a wide range of voltage. On the other hand, where the output of the temperature measurement power supply 233, which is constant at all times, is used, as in the present embodiment, the signal detection circuit 240 can easily detect a voltage with high accuracy. In the present embodiment, the output current of the heater power supply 231 for heating the heater 160 and the output current of the temperature measurement power supply 233 are combined and pass through the same path, but the frequencies of the two output signals are different. Therefore, the signals are separated from each other owing to this frequency difference.

[First Modification of First Embodiment]

Figure 10:
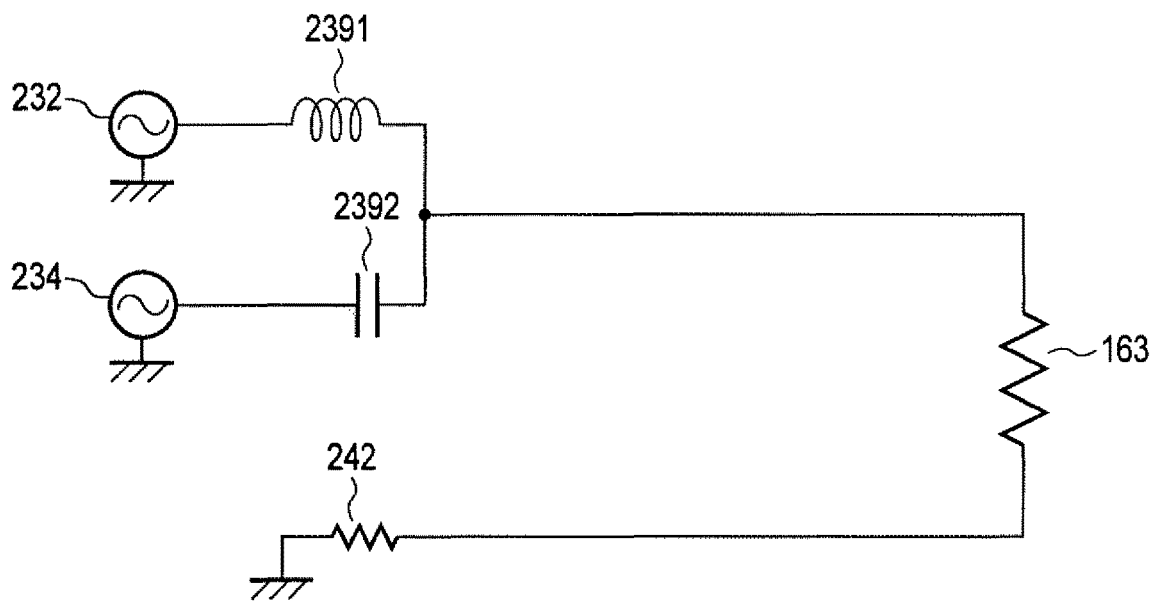
FIG. 10 is a diagram schematically showing an example of an electric circuit of the heater of a surgical system according to the first modification of the first embodiment.

The first modification of the first embodiment will be described. In the description below, reference will be made to how the first modification differs from the first embodiment. Therefore, the same symbols will be used to denote structural elements similar or corresponding to those of the first embodiment, and a description of such structural elements will be omitted. In the above-mentioned embodiment, the first frequency, which is the output frequency of the first power supply 232 of the heater power supply 231, is higher than the second frequency, which is the output frequency of the second power supply 234 of the temperature measurement power supply 233. Conversely, the first frequency may be lower than the second frequency, as in the present modification. In this case, as shown in FIG. 10, a third inductor 2391 is connected to the output terminal of the first power supply 232, and a third capacitor 2392 is connected to the output terminal of the second power supply 234. In this case, where the frequency separation unit 252 is configured as a filter circuit 253, the filter circuit 253 is a high-pass filter. Where the frequency separation unit 252 is realized by using such an arithmetic operation as fast Fourier transform or wavelet transform performed by the arithmetic circuit 251, a second frequency higher than the first frequency is extracted by the operation.

Furthermore, the first frequency or the second frequency may be zero, that is, the output of the first power supply 232 or the second power supply 234 may be a direct current. In this case, the frequency of the direct-current output of either the first power supply 232 or the second power supply 234 is lower than the frequency of the other output.

According to this modification as well, the same advantages as those of the first embodiment can be obtained.

[Second Modification of First Embodiment]

Figure 11:
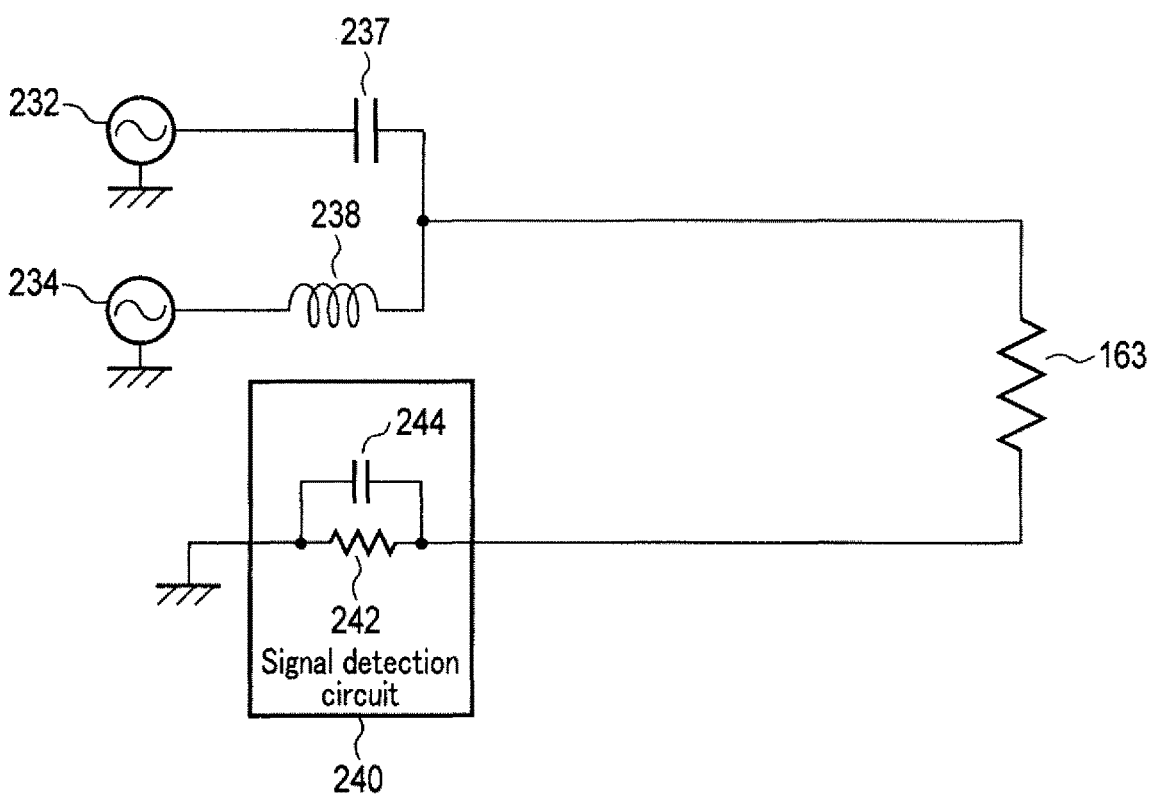
FIG. 11 is a diagram schematically showing an example of an electric circuit of the heater of a surgical system according to the second modification of the first embodiment.

The second modification of the first embodiment will be described. In the description below, reference will be made to how the second modification differs from the first embodiment. Therefore, the same symbols will be used to denote structural elements similar or corresponding to those of the first embodiment, and a description of such structural elements will be omitted. In the present modification, as shown in FIG. 11, a sensing capacitor 244 is provided in parallel with the sensing resistor 242 in the signal detection circuit 240. FIG. 12 shows an equivalent circuit of the first power supply 232 that produces an output having a high-frequency first frequency in such a circuit configuration. Since the first frequency is a high frequency, a current passes through the sensing capacitor 244 in the signal detection circuit 240. On the other hand, FIG. 13 shows an equivalent circuit of the second power supply 234 that produces an output having a low-frequency second frequency. Since the second frequency is a low frequency, a current passes through the sensing resistor 242 in the signal detection circuit 240.

In the signal detection circuit 240 of the present modification, a voltage detected by use of the sensing resistor 242 is a voltage related to the output from the second power supply 234. In the case of this modification, therefore, the frequency separation unit 252 does not have to be provided in the resistance value calculation circuit 250. In this modification, the signal detection circuit 240 functions as a frequency separation unit.

According to this modification as well, a resistance voltage having the second frequency can be acquired, so that the heater resistance Rheat can be easily obtained. In particular, in the present modification, the need for the frequency separation unit 252 can be eliminated by merely inserting the sensing capacitor 244 in parallel with the sensing resistor 242, so that the system configuration can be simplified.

It is to be noted that the present modification can also be put into practice where the output of the second power supply 234 is a direct current.

Second Embodiment

The second embodiment will be described. In the description below, reference will be made to how the second embodiment differs from the first embodiment. Therefore, the same symbols will be used to denote structural elements similar or corresponding to those of the first embodiment, and a description of such structural elements will be omitted. In the present embodiment, a heater resistance is calculated more accurately than in the first embodiment, in consideration of the value of the contact resistance between the power supply device connector 285 and the cable connector 195.

Figure 14:
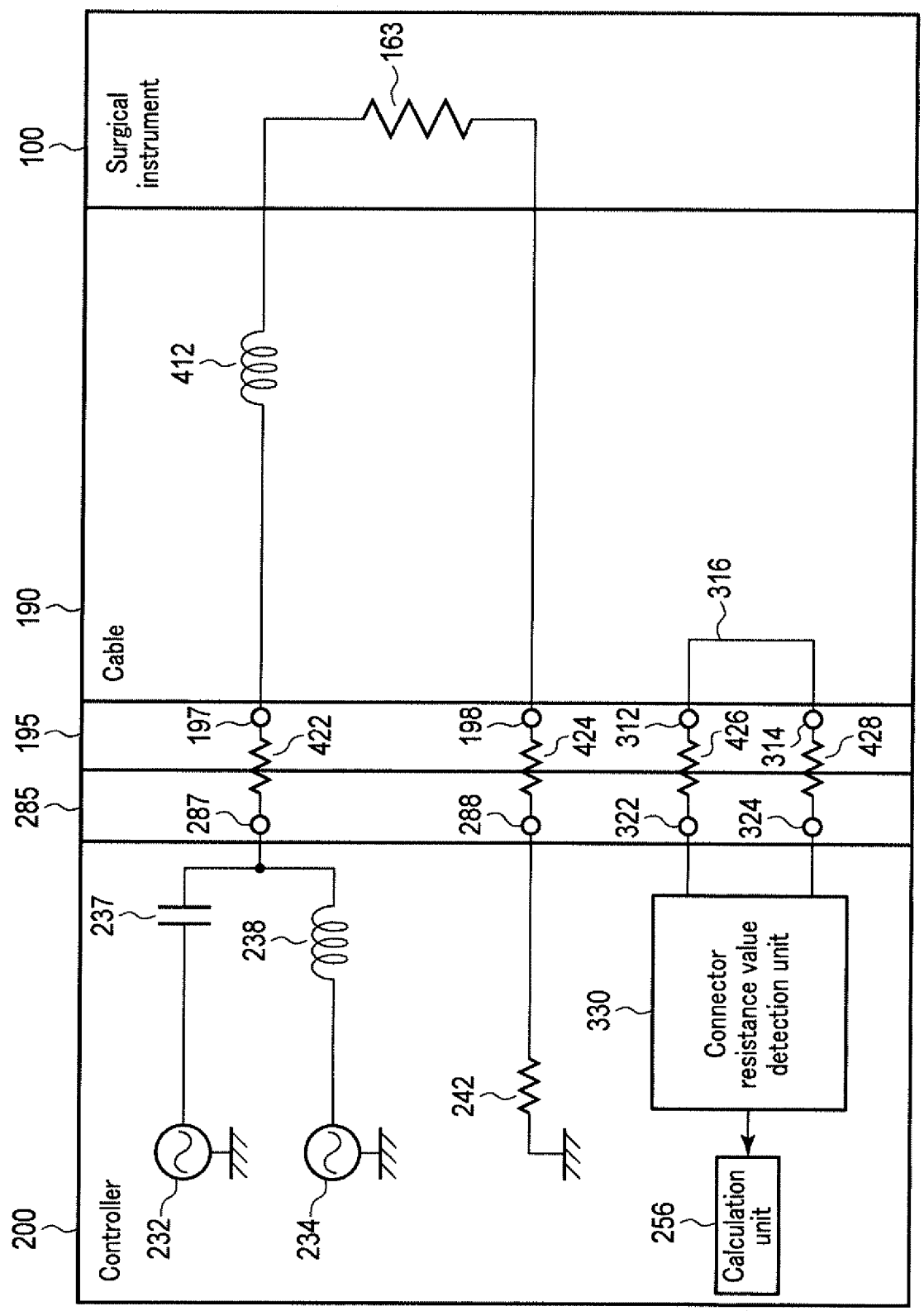
FIG. 14 is a diagram schematically showing a configuration example of a surgical system according to the second embodiment.

FIG. 14 schematically illustrates a configuration example of the surgical system 1 according to the second embodiment. The resistance of the contact point between the third terminal 287 and the first terminal 197 is referred to as a first connector resistance 422, and the resistance of the contact point between the fourth terminal 288 and the second terminal 198 is referred to as a second connector resistance 424.

The contact point between the power supply device connector 285 and the cable connector 195 changes in accordance with the number of times of use. At this time, the change at the third terminal 287 and the change at the fourth terminal 288 have the same tendency. Likewise, the change at the first terminal 197 and the change at the second terminal 198 have the same tendency.

In the present embodiment, therefore, the cable connector 195 is provided with, in addition to the first terminal 197 and the second terminal 198, a fifth terminal 312 and a sixth terminal 314 having similar configurations to those of the first terminal 197 and the second terminal 198. Similarly, the power supply device connector 285 is provided with, in addition to the third terminal 287 and the fourth terminal 288, a seventh terminal 322 and an eighth terminal 324 having similar configurations to those of the third terminal 287 and the fourth terminal 288. The fifth terminal 312 and the sixth terminal 314 are connected by a conducting wire 316. When the cable connector 195 is connected to the power supply device connector 285, the fifth terminal 312 and the seventh terminal 322 are connected to each other, and the sixth terminal 314 and the eighth terminal 324 are connected to each other.

The controller 200 is provided with a connector resistance value detection unit 330. The seventh terminal 322 and the eighth terminal 324 are connected to the connector resistance value detection unit 330. The connector resistance value detection unit 330 detects a resistance value between the seventh terminal 322 and the eighth terminal 324. The connector resistance value detection unit 330 transmits the detected resistance value to the calculation unit 256.

Where the cable connector 195 is connected to the power supply device connector 285, the contact resistance between the seventh terminal 322 and the fifth terminal 312 is referred to as a third connector resistance 426, and the contact resistance between the eighth terminal 324 and the sixth terminal 314 will be referred to as a fourth connector resistance 428. Where the cable connector 195 is connected to the power supply device connector 285, the connector resistance value detection unit 330 acquires a resistance value of the circuit constituted by the seventh terminal 322, the fifth terminal 312, the conducting wire 316, the sixth terminal 314 and the eighth terminal 324. That is, the connector resistance value detection unit 330 detects a resistance value including the third connector resistance 426 and the fourth connector resistance 428. The connector resistance value detection unit 330 transmits the detected resistance value to the calculation unit 256.

The resistance values of the first connector resistance 422 and the second connector resistance 424 are substantially equal to the resistance values of the third connector resistance 426 and the fourth connector resistance 428. Therefore, the calculation unit 256 can regard the obtained resistance value as the sum of the first connector resistance 422 and the second connector resistance 424. The sum of the first connector resistance 422 and the second connector resistance 424 will be referred to as a connector resistance Rcon.

The calculation unit 256 can calculate a corrected heater resistance Rheat_c corrected with the value of the connector resistance Rcon, by the following:

$$Rheat\_c = Rheat - Rcon$$

The calculation unit 256 transmits the corrected heater resistance Rheat_c to the output control circuit 220. The output control circuit 220 calculates a heater temperature using the corrected heater resistance Rheat_c. As a result, where the heater temperature is calculated using the corrected heater resistance Rheat_c, it can be calculated more accurately than in the case where it is calculated using the heater resistance Rheat.

According to the present embodiment, the controller 200 can control the temperature of the heater 160 of the surgical instrument 100 with higher accuracy than in the first embodiment.

Third Embodiment

The third embodiment will be described. In the description below, reference will be made to how the third embodiment differs from the first embodiment. Therefore, the same symbols will be used to denote structural elements similar or corresponding to those of the first embodiment, and a description of such structural elements will be omitted. In the second embodiment described above, as a parasitic resistance, only the connector resistance Rcon is taken into consideration and corrected. In the present embodiment, the calculation unit 256 can calculate a heater resistance by further correcting the cable resistance Rcab, which is the parasitic resistance of the cable 190.

FIG. 15 schematically shows a circuit configuration of the surgical system 1 according to the present embodiment. In the present embodiment, the cable resistance 432, which is the parasitic resistance of the cable 190, is taken into consideration. The surgical instrument 100 of the present embodiment has a switch 182. The switch 182 is a switch for switching between a first state in which the heater resistor 163 is inserted between the first terminal 197 and the second terminal 198 and a second state in which the first terminal 197 and the second terminal 198 are short-circuited, with the heater resistor 163 bypassed.

In the present embodiment, the switch 182 is set in the second state in the initial setting state, which is the state before the treatment is started. In this state, the resistance value calculation circuit 250 acquires a resistance value between the third terminal 287 and the fourth terminal 288. This resistance value is the sum of the connector resistance Rcon and the cable resistance Rcab.

At the time of treatment, the switch 182 is set in the first state, and the surgical system 1 functions in the same way as in the first embodiment. In the present embodiment, the calculation unit 256 can calculate a corrected heater resistance Rheat_c, as below, using the sum of the connector resistance Rcon and the cable resistance Rcab obtained in the initial setting state.

$$Rheat\_c = Rheat - Rcon - Rcab$$

According to the present embodiment, the temperature of the heater 160 of the surgical instrument 100 can be controlled with higher accuracy than in the second embodiment.
[First Modification of Third Embodiment]

The first modification of the third embodiment will be described. In the description below, reference will be made to how the first modification differs from the third embodiment. Therefore, the same symbols will be used to denote structural elements similar or corresponding to those of the third embodiment, and a description of such structural elements will be omitted. In the third embodiment, in order to bypass the heater resistor 163, the switch 182 is used to switch between the first state and the second state. In this modification, a variable resistor 184 is provided in parallel with the heater resistor 163 in the surgical instrument 100, as shown in FIG. 16.

In the present embodiment as well, the sum of the connector resistance Rcon and the cable resistance Rcab is measured, with the resistance value of the variable resistor 184 being sufficiently lowered in the initial setting state before the start of treatment. On the other hand, at the time of treatment, the resistance value of the variable resistor 184 is made sufficiently high. The other points are the same as those of the third embodiment. According to this modification as well, the temperature of the heater 160 of the surgical instrument 100 can be controlled with high accuracy.
[Second Modification of Third Embodiment]

Figure 17:
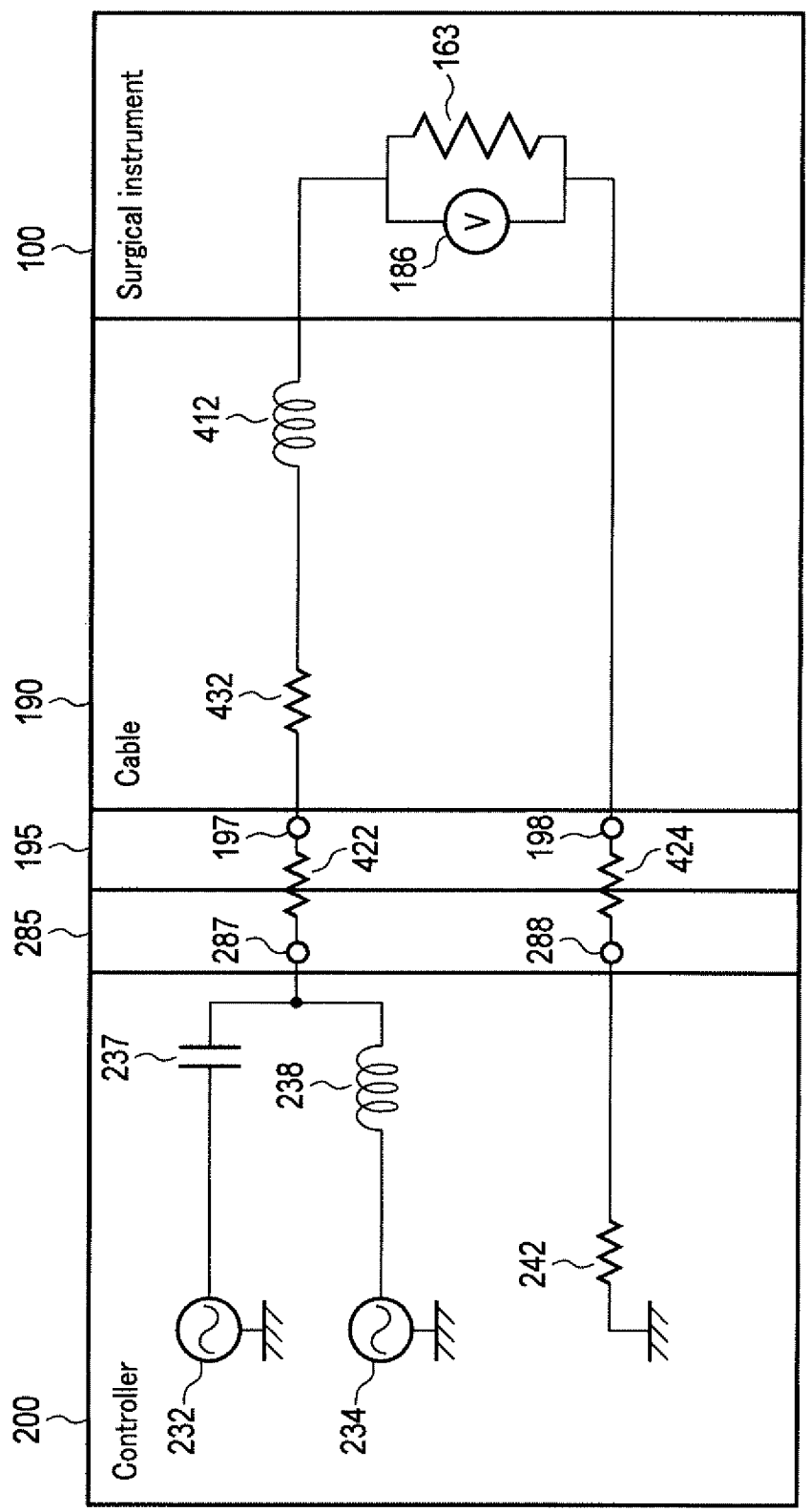
FIG. 17 is a diagram schematically showing a configuration example of a surgical system according to the second modification of the third embodiment.

The second modification of the third embodiment will be described. In the description below, reference will be made to how the second modification differs from the third embodiment. Therefore, the same symbols will be used to denote structural elements similar or corresponding to those of the third embodiment, and a description of such structural elements will be omitted. In this modification, a voltage detection unit 186 is provided in the surgical instrument 100, as shown in FIG. 17. The voltage detection unit 186 detects a potential difference between both ends of the heater resistor 163. That is, the voltage detection unit 186 can acquire a resistance value of the heater resistor 163, with the sum of the connector resistance Rcon and the cable resistance Rcab being excluded. According to this modification as well, the temperature of the heater 160 of the surgical instrument 100 can be controlled with high accuracy.

Fourth Embodiment

The fourth embodiment will be described. In the description below, reference will be made to how the fourth embodiment differs from the second embodiment. Therefore, the same symbols will be used to denote structural elements similar or corresponding to those of the third embodiment, and a description of such structural elements will be omitted. FIG. 18 schematically illustrates a configuration example of the surgical system 1 according to the present embodiment. In the third embodiment described above, only the connector resistance Rcon of the parasitic resistance (the first connector resistance 422 and the second connector resistance 424) and the cable resistance Rcab (the cable resistance 432) are taken into consideration and corrected. In the present embodiment, the calculation unit 256 can calculate the heater resistance 163 by further correcting the parasitic capacitance 414 of the cable 190.

As shown in FIG. 18, a connector resistance Rcon (a first connector resistance 422 and a second connector resistance 424) and a cable resistance Rcab (cable resistance 432) are calculated by the same means as used in the second embodiment. That is, a conducting wire 316 extending to the inside of the surgical instrument is connected to a parasitic resistance value detecting section 331, which corresponds to the connector resistance value detection unit 330 of the second embodiment. In addition to the third connector resistance 426 and the fourth connector resistance 428, the parasitic resistance value detecting section 331 also acquires a resistance value including a second cable resistance 433 corresponding to the cable resistance 432. Therefore, in addition to the connector resistance Rcon (the first connector resistance 422 and the second connector resistance 424), the parasitic resistance value detecting section 331 can also calculate a cable resistance Rcab (cable resistance 432).

Furthermore, in the present embodiment, the parasitic capacitance 414 is corrected using the detection values of the first power supply 232 and the second power supply 234 and the frequency difference between the detection values. A corrected heater resistance Rheat_c is expressed by mathematical formula 1 below, $$Rheat\_c = \frac{\frac{1}{f1^2} - \frac{1}{f2^2}}{\frac{1}{\left(\frac{V1}{I1}\cos(\alpha 1) - Rcab - Rcon - Rdet\right)f1^2} - \frac{1}{\left(\frac{V2}{I2}\cos(\alpha 2) - Rcab - Rcon - Rdet\right)f2^2}}$$

where V1 is a first power supply voltage, I1 is a first power supply current, α1 is a phase difference between the first power supply voltage V1 and the first power supply current I1, f1 is a first power supply frequency, V2 is a second power supply voltage, I2 is a second power supply current, α2 is a phase difference between the second power supply voltage V2 and the second power supply current I2, and f2 is a second power supply frequency. A corrected heater resistance Rheat_c can be calculated with higher accuracy by using the two frequency differences. Therefore, the temperature of the heater 160 can be detected more accurately.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A control device for a surgical instrument including a heater having a first end and a second end and configured to generate heat in response to power supplied thereto, the control device comprising:
    a first power supply configured to output a first current having a first frequency and supplied to the first end of the heater for causing the heater to generate heat;
    a second power supply configured to output a second current combined with the first current, supplied to the first end of the heater through a common path and having a second frequency different from the first frequency;
    a resistance value calculation circuit configured to separate a signal component related to the second current from the first and second currents having passed through the heater, and to calculate a heater resistance value, which is a resistance value of the heater, based on the signal component, wherein the resistance value calculation circuit includes a signal detection circuit including a sensing resistor provided in series with the second end of the heater and a sensing capacitor provided in parallel with the sensing resistor and calculates the heater resistance value based on a potential difference between both ends of the sensing resistor, an output voltage of the second power supply, and a resistance value of the sensing resistor; and
    an output control circuit configured to control an output of the first power supply to adjust a temperature of the heater based on the calculated heater resistance value.

2. The control device according to claim 1, wherein the first current and the second current are both alternating currents.

3. The control device according to claim 2, wherein the resistance value calculation circuit calculates the heater resistance value, with phase information included in the signal component being removed.

4. The control device according to claim 1, wherein the first frequency is higher than the second frequency.

5. The control device according to claim 1, wherein one of the first current and the second current is an alternating current, and a remaining one thereof is a direct current.

6. The control device according to claim 4, wherein the second current is a direct current.

7. The control device according to claim 1, wherein the resistance value calculation circuit includes a filter circuit, and
    the filter circuit separates the signal component related to the second current from the first current and the second current passed through the first end of the heater.

8. The control device according to claim 1, wherein a current value of the second current is smaller than a current value of the first current.

9. The control device according to claim 1, wherein the first frequency is 10 times or more the second frequency.

10. A surgical system comprising:
    a control device as defined in claim 1; and
    a surgical instrument including a heater configured to generate heat in response to power supplied from the control device.

11. The control device according to claim 7, wherein the filter circuit includes a low-pass filter, and the first frequency is higher than the second frequency.

12. The control device according to claim 1, wherein the resistance value calculation circuit includes a frequency separation unit, and the frequency separation unit separates the signal component related to the second current from the first current and the second current passed through the first end of the heater by fast Fourier transform or wavelet transform.

* * * * *